United States Patent
Kwon et al.

(10) Patent No.: US 9,976,118 B2
(45) Date of Patent: May 22, 2018

(54) METHOD FOR INDUCING TAILORED PLURIPOTENT STEM CELLS USING EXTRACT OF PLANT STEM CELLS OR PLANT DEDIFFERENTIATED STEM CELLS, AND PLURIPOTENT STEM CELLS PRODUCED BY MEANS OF THE METHOD

(71) Applicant: SNU R&DB FOUNDATION, Seoul (KR)

(72) Inventors: Yoo-Wook Kwon, Seoul (KR); Young-Bae Park, Seoul (KR); Hyo-Soo Kim, Seoul (KR); Jae-Seung Paek, Gunpo-si (KR)

(73) Assignee: SNU R&DB FOUNDATION, Seoul (KR)

( * ) Notice: Subject to any disclaimer, the term of this patent is extended or adjusted under 35 U.S.C. 154(b) by 0 days. days.

(21) Appl. No.: 14/762,773

(22) PCT Filed: Jan. 28, 2014

(86) PCT No.: PCT/KR2014/000770
§ 371 (c)(1),
(2) Date: Jul. 22, 2015

(87) PCT Pub. No.: WO2014/119893
PCT Pub. Date: Aug. 7, 2014

(65) Prior Publication Data
US 2015/0361391 A1  Dec. 17, 2015

(30) Foreign Application Priority Data
Jan. 30, 2013 (KR) ........................ 10-2013-0010559

(51) Int. Cl.
*C12N 5/00* (2006.01)
*C12N 5/074* (2010.01)
*A61K 8/97* (2017.01)
*A61Q 19/00* (2006.01)
*A61K 8/99* (2017.01)

(52) U.S. Cl.
CPC .............. *C12N 5/0607* (2013.01); *A61K 8/97* (2013.01); *A61K 8/99* (2013.01); *A61Q 19/00* (2013.01); *C12N 5/0696* (2013.01); *A61K 2800/86* (2013.01); *C12N 2500/76* (2013.01); *C12N 2501/998* (2013.01)

(58) Field of Classification Search
None
See application file for complete search history.

(56) References Cited

FOREIGN PATENT DOCUMENTS

| CN | 102382798 A | 3/2012 |
|---|---|---|
| CN | 102803473 A | 11/2012 |
| JP | 2011-016760 A | 1/2011 |
| KR | 10-2009-0115394 A | 11/2009 |
| KR | 10-2009-0130582 A | 12/2009 |
| KR | 10-2011-0033047 A | 3/2011 |
| KR | 10-2012-0058829 A | 6/2012 |

OTHER PUBLICATIONS

Sequoia, Wikipedia 2016.*
Pera et al, J Cell Sci 2000;113:5-10.*
Malik et al. in Methods in Molecular Biology 2013, vol. 97, Lakshmipathy eds Springer Sci.*
Nester et al. BioMed Central 2013;4:37, pp. 1-7.*
Serafini and Verfaillie, Semi Reprod Med 2006;24:379-88.*
Reynertson et al. Exp Cell Res 2011;317:82-93.*
Sugimoto et al. Trends Cell Biol 2011;21:212-8.*
Hill et al. J Invest Dermatol 2011;131(2):abstract #483.*
Xu et al., "ES Cell Extract-Induced Expression of Pluripotent Factors in Somatic Cells", The Anatomical Record, Aug. 2009, vol. 292, No. 8, pp. 1229-1234.
Bru et al., "Rapid induction of pluripotency genes after exposure of human somatic cells to mouse ES cell extracts", Experimental Cell Research, Aug. 15, 2008, vol. 314, No. 14, pp. 2634-2642.
International Search Report dated May 26, 2014 of PCT/KR2014/000770 which is the parent application and its English translation—4 pages.
Office action dated Dec. 5, 2016 of corresponding Chinese Patent Application No. 201480006854.9—6 pages.

* cited by examiner

*Primary Examiner* — Janice Li
(74) *Attorney, Agent, or Firm* — Knobbe Martens Olson & Bear LLP

(57) ABSTRACT

A method for inducing tailored pluripotent stem cells by reprogramming differentiated cells of an adult by using an extract of plant stem cells and plant dedifferentiated stem cells (callus); pluripotent stem cells produced by means of the method; and a cell therapy agent comprising the pluripotent stem cells are disclosed. It is possible to overcome ethical problems since eggs are not used in the making of pluripotent stem cells having abilities like embryonic stem cells. It is possible to produce pluripotent stem cells of ensured safety because a plant stem cell extract which above all has been verified to be harmless to the body is used. It is possible to develop an immunocompatible cell therapy agent tailored to different individuals.

14 Claims, 7 Drawing Sheets

Day 5 human-derived pluripotent stem cells

A.

Day 32 human-derived pluripotent stem cells

B.

human embryonic stem cells

A.  Day 50 human pluripotent stem cells induced according to the method of the present invention(left)
were observed to be positive to alkaline phosphatase B.  Day 50 human pluripotent stem cells induced by the virus (left)
were observed to be positive to alkaline phosphatase staining (right).

gene expression of the pluripotent stem cells hES : human ES cells
hiPS ; human iPS cells by plant stem cell extract

METHOD FOR INDUCING TAILORED PLURIPOTENT STEM CELLS USING EXTRACT OF PLANT STEM CELLS OR PLANT DEDIFFERENTIATED STEM CELLS, AND PLURIPOTENT STEM CELLS PRODUCED BY MEANS OF THE METHOD

The present invention was undertaken with the support of Bio and Medical Technology Development Program of the National Research Foundation (NRF) No. NRF-2015M3A9B4051041 grant funded by the ministry of science, ICT and Future Planning, Innovative Research Institute for Cell Therapy No. A062260 grant funded by the Ministry of Health and Welfare, Korea Health Technology R&D Project No. HI14C1277 grant funded by the Ministry of Health and Welfare, and Advanced medical technologies development program through the Korea Health Industry Development Institute (KHIDI) No. HI14C1541 grant funded by the Ministry of Health and Welfare.

TECHNICAL FIELD

The present invention relates to a method of inducing customized pluripotent stem cells by reprogramming and/or dedifferentiating differentiated cells of an adult by using an extract of plant stem cells and/or plant dedifferentiated stem cells, pluripotent stem cells produced using the method; and a cell therapy agent including the pluripotent stem cells.

BACKGROUND ART

A stem cell is a generic name for an undifferentiated type of cell found in tissues of embryos, fetuses and adults, which is characterized by the ability to differentiate into a diverse range of specialized cell types. In various classifications of stem cells, pluripotent stem cells refer to cells which may differentiate into cells derived from any of the three germ layers constituting the living body.

In the classification, stem cells may be classified according to an anatomical region, the function of cells, the type of antigen expressed on the cell surface, a transcription factor, a protein generated by cells and the type of specific cells which may be generated by the stem cells.

One of the most frequently used criteria is a source from which stem cells are derived. The stem cells may be classified into embryonic stem cells (ES cells) which are isolated from an embryo, and adult stem cells that are isolated from an adult.

According to another frequently used classification of the number of types of cells differentiated from a stem cell, stem cells may be classified into pluripotent stem cells, multipotent stem cells, and unipotent stem cells. In general, embryonic stem cells are representative of pluripotent stem cells, and adult stem cells are separated into multipotent stem cells and unipotent stem cells.

The inner cell mass of a blastocyst which is formed in the early development of mammals after fertilization is a part which subsequently forms the embryo, and embryonic stem cells formed from the inner cell mass may be referred to as pluripotent stem cells having the potential to differentiate into cells of all tissues constituting the individual. That is, the embryonic stem cells are undifferentiated cells which are able to proliferate without limitation, differentiate into all types of cells, also form germ cells in contrast to adult stem cells, and thus may be inherited by the next generation.

However, the preparation of these embryonic stem cells, that is, pluripotent stem cells results in the destruction of the human embryo, which raises religious and ethical issues. Further, since embryonic stem cells are derived from limited embryos, there is a lack of immune compatibility between each individual, and thus there may be transplant rejection in the development of embryonic stem cells as cell therapeutics. In order to address these issues, there have been various attempts to artificially produce pluripotent stem cells mimicking embryonic stem cells by using adult-derived cells.

Examples of the representative methods include somatic cell nuclear transfer (SCNT), fusion with ES cell, reprogramming by defined factor, etc. SCNT requires a large amount of oocytes due to the very low efficiency thereof. Fusion with ES cells has a problem in stability because the pluripotent cells induced thereby contain two additional pairs of genes. Reprogramming by defined factors, which is the most recent technique, employs a virus containing an oncogene, and thus may cause tumorigenicity.

In order to ensure customized pluripotent stem cells for the development of cell therapeutics, there is a need for the development of a method of producing pluripotent stem cells which is safe and may address the ethical issues. According to this need, the inventors of the present invention have developed dedifferentiated stem cells using an extract of induced pluripotent stem cells (iPS) derived from animals, but there are some restrictions thereof.

First, about 20 mg or more of an iPS extract is required to perform the above-described method. Accordingly, the dedifferentiation induction in which an extract is isolated from human dedifferentiated stem cells, which requires much cost and labor, has not yet succeeded. For example, those skilled in the art have to spend 3 months or more to prepare human dedifferentiated stem cells to obtain 20 mg of an extract, requiring a high cost.

Second, animal stem cells or dedifferentiated stem cells corresponding thereto are not completely crushed and are remained in the process of separating the extract, when somatic cells to be induced to dedifferentiate are treated with the extract, it is difficult to distinguish cells induced to dedifferentiate from dedifferentiated stem cells remaining in the extract, and thus it may not be immediately determined whether the experiment succeeded or not, and may be determined after analyzing the genomic DNA thereof. Accordingly, a lot of time and cost may be wasted.

Third, since there have been rare cases of human dedifferentiated stem cells produced using proteins, an extract of human dedifferentiated stem cells produced using a virus is used. However, this extract may contain cancer-causing substances induced by the virus, which may be an obstacle to clinical application.

DISCLOSURE

Technical Problem

The present invention is developed to address the issues of the conventional techniques as described above, and there is provided a method of preparing customized pluripotent stem cells which ensure safety and have no ethical problem. Further, there is provided a method of inducing human dedifferentiated stem cells, which is difficult to be implemented by the conventional technique.

The inventors of the present invention have developed a method of inducing pluripotent stem cells having the same genetic background as that of an adult from which cells are isolated, by using adult-derived cells. Accordingly, the inventors will propose that the method according to the embodiment of the present invention is suitable for producing pluripotent stem cells by delivering the identical results as from adult-derived cells having various genetic backgrounds.

Technical Solution

In order to resolve the above-described technical subject, the present invention provides a method of inducing pluripotent stem cells by using an extract from plant-derived stem cells.

More specifically, the present invention provides a method of producing a customized pluripotent stem cell, including: producing an extract from any of plant stem cells or induced pluripotent plant stem cells; introducing the extract into adult-derived cells; and culturing the adult-derived cells to produce pluripotent stem cells having the same pluripotency as that of embryonic stem cells.

The extract includes proteins, lipids, sugars and acids obtained from plant cells.

The extract includes a callus powder.

According to an embodiment of the present invention, the present invention further includes treating the extract of step a) with a culture medium before the introduction of the extract into the adult-derived cells.

According to another embodiment of the present invention, the present invention may further include treating the adult-derived cells with a membrane permeability-promoting component before the introduction of the extract into the adult-derived cells. The membrane permeability-promoting component may be a protein or a compound, which include streptolysin O and digitonin.

According to still another embodiment of the present invention, the present invention may further include transferring and culturing the adult-derived cells into which the extract is introduced onto a feeder cell layer. The feeder cell may include STO cells.

Further, the present invention provides a method of producing a customized pluripotent stem cell, including: producing an extract from any of plant stem cells or induced pluripotent plant stem cells; introducing the extract into adult-derived cells; and culturing the adult-derived cells in a general cell culture, transferring the adult-derived cells onto a feeder cell layer, and culturing the adult-derived cells in an embryonic stem cell medium.

Further, the present invention provides pluripotent stem cells prepared using the above-described method, which are very similar to embryonic stem cells.

Further, the present invention provides a cell therapy agent including the pluripotent stem cells.

Further, the present invention provides a method of treating a disease, which includes administering a pharmaceutically effective amount of the cell therapy agent.

Further, the present invention provides the use of the pluripotent stem cells as an effective component of the cell therapy agent.

Advantageous Effects

According to the embodiment of the present invention, an extract from plant stem cells or induced pluripotent plant stem cells can be used as the most effective method of producing customized stem cells. Further, this method will be a production method which can be used in the wide range covering all types of cells including humans having various genetic backgrounds. Moreover, the method according to the embodiment of the present invention employs an extract from plant-derived stem cells, and thus allows for the production of customized pluripotent stem cells which raise no ethical issue and ensure safety.

Figure 4:
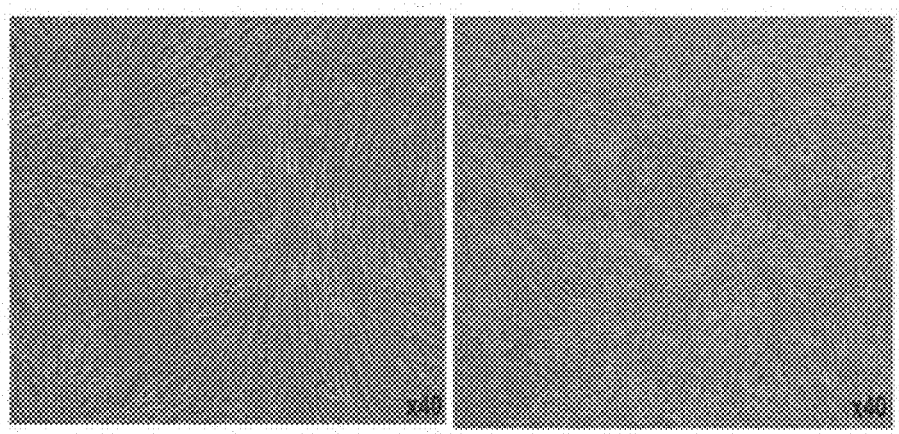
Figure 4:
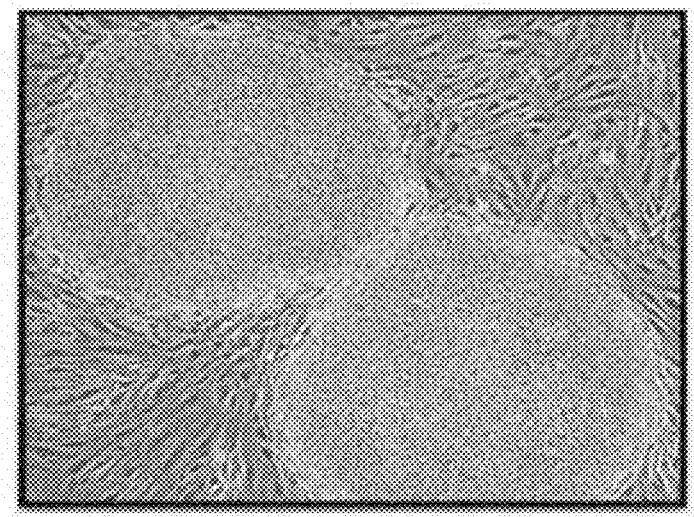

A of FIG. 4 is a view of induced pluripotent stem cells on day 32 after treatment with an extract of plant stem cells and after being transferred onto a feeder cell layer and subcultured 4 times. B of FIG. 4 is a view illustrating typical embryonic stem cells.

Figure 5:
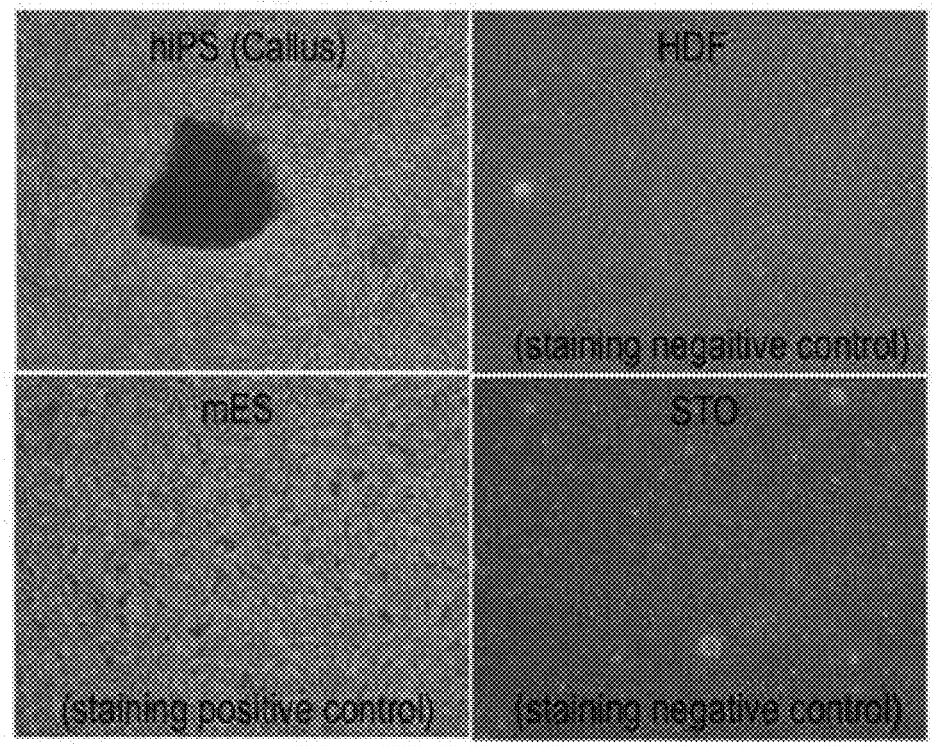

FIG. 5 is a view illustrating the alkaline phosphatase test result of induced pluripotent stem cells on day 32 after treatment with an extract of plant stem cells and after being transferred onto a feeder cell layer and subcultured 4 times.

Figure 6:
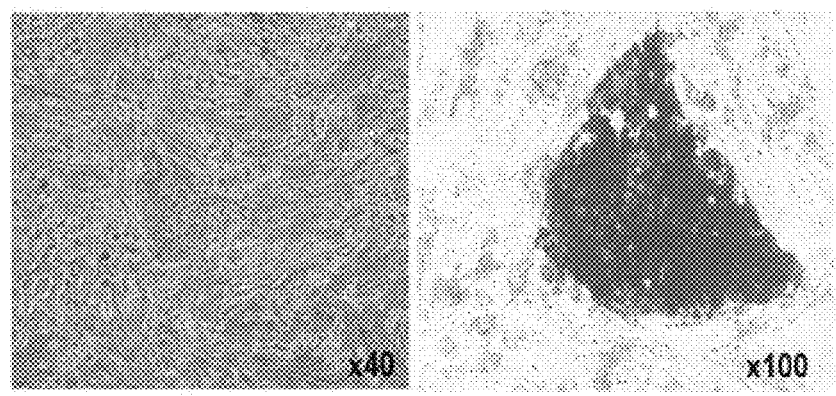
Figure 6:
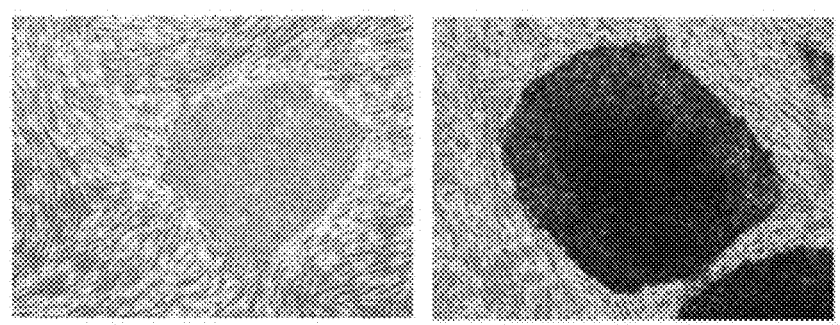

A of FIG. 6 is a view (left) illustrating induced pluripotent stem cells on day 50 after treatment with an extract of plant stem cells and after being transferred onto a feeder cell layer and subcultured 7 times and a view (right) illustrating the alkaline phosphatase test result thereof. B of FIG. 6 is a view (left) illustrating human pluripotent stem cells induced through the viral delivery of four Yamanaka factors and a view (right) illustrating the alkaline phosphatase test result thereof.

Figure 7:
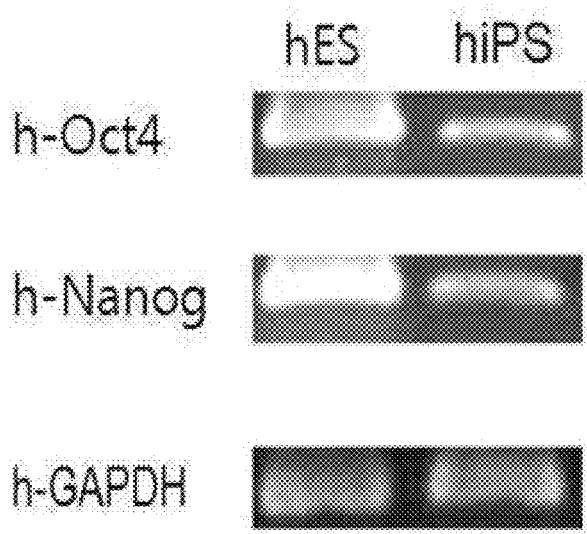

FIG. 7 is a view illustrating the gene expression of the induced pluripotent stem cells according to the method of the present invention.

MODES OF THE INVENTION

In order to achieve the objective of the present invention, the present invention provides a method of producing a customized pluripotent stem cell, including: a) producing an extract from any of plant stem cells or induced pluripotent plant stem cells; b) introducing the extract into adult-derived cells; and c) culturing the adult-derived cells to produce pluripotent stem cells having the same pluripotency as that of embryonic stem cells.

The extract may include proteins, lipids, sugars, acids and organic compounds obtained from plant cells, but is not limited thereto.

The extract may include a callus powder, and the callus powder is preferably used by dissolving in water, but the present invention is not limited thereto.

The term "stem cell", as used herein, refers to a master cell which may be reproduced without limitation so to form specialized cells of tissues and organs. The stem cell denotes pluripotent or multipotent cells which may be developed. The stem cells may be differentiated into two daughter stem cells or one daughter stem cell and one derived (transit) cell, followed by the proliferation into cells in a matured and complete form of tissues.

The term "embryonic stem cell", as used herein, refers to a cell with pluripotency, which is prepared by isolating and culturing from the inner cell mass of the blastocyst which is formed in the early development of mammals after fertilization As used herein, the term "extract from dedifferentiated stem cell or induced pluripotent stem cell (iPS)" refers to a material obtained by grinding dedifferentiated stem cells or induced pluripotent stem cells (iPS) which are induced and cultured using a diversity of methods in vitro through a physicochemical method, and separating them by centrifugation, etc.

As used herein, the term "plant stem cell" is a plant stem cell derived from a cambium. Especially, plant stem cells include cambial meristematic cells (CMCs) which are not physically damaged in a cambium interposed at the boundary between the xylem and phloem of plants.

As used herein, the term "callus" (callus tissue, wound tissue or wound-healing tissue) refers to an undifferentiated amorphous cell mass, and mainly refers to a tumor tissue formed by meristematic tissues around a wound when a plant is wounded. Plants are mainly constituted of meristematic tissues in which cells are divided and permanent tissues with no cell division. When a cell of initial meristematic tissues is cultured in a nutrient medium, a callus is formed. Thereafter, an embryoid is formed and differentiated into a plant. The callus is often referred to as a "stem cell of plant". The type of the callus used in the present invention is not limited.

The term "pluripotent stem cell", as used herein, refers to a stem cell with multipotency (pluripotency) and capable of differentiating into any of the three germ layers, that is, the endoderm, mesoderm and ectoderm. Conventionally, embryonic stem cells are representative of pluripotent stem cells.

The term "customized pluripotent stem cell", as used herein, refers to a pluripotent stem cell genetically consistent with a donor cell used to produce the pluripotent stem cell, meaning that the pluripotent stem cell is derived from the donor cell.

The term "adult-derived cell", as used herein, is a term contrary to an embryonic cell, and refers to a cell derived from an adult living after birth.

The term "differentiation," as used herein, refers to a process by which during the division, proliferation and growth thereof, a cell becomes specialized in structure and function, that is, a cell changes its morphology or function so as to perform a given task. In general, differentiation denotes a phenomenon in which a relatively simple system is divided into two or more partial systems which are qualitatively different. For example, "differentiation" denotes that the portions of the biosystem which are homogeneous at first gain a qualitative difference, like that the portions of an egg, which are initially homogeneous in its ontogeny, gain a distinction such as a head, a body or the like, or cells are classified into myocyte, neuron or the like, or refers to a state in which the portions are consequently divided into areas or partial systems which may be distinguished qualitatively.

The method according to the embodiment of the present invention includes culturing plant stem cells or all types of induced pluripotent stem cells induced using various methods, and producing an extract therefrom, which may be performed using a general method well-known in the related field. For example, a protein derived from each cell may be extracted by culturing plant stem cells or all types of induced pluripotent stem cells induced using various methods, treating with a protease, and collecting the suspension or reacting plant-derived stem cells at 65° C. for 2 hours to filter. A callus powder may be used in the embodiment of the present invention.

Regarding the production of the extract, those skilled in the art may easily appreciate that extracts having a high concentration may be produced using an existing extraction method. The concentration of the extract is preferably in the range of 100 ug/ml to 1 mg/ml, and more preferably, is 500 ug/ml. When the concentration of the extract is out of the above-described range, the effect of inducing the customized pluripotent stem cells is reduced, or the extracted cells may be dead.

The method according to the embodiment of the present invention includes introducing the extract isolated from plant stem cells or all types of induced pluripotent stem cells induced using various methods into adult-derived cells.

The adult-derived cells include a human dermal fibroblast.

For the introduction, cells are treated with a membrane permeability-promoting component (e.g., streptolysin O or digitonin) to form a reversible small hole (permeabilization), such that the extract may flow into the cells. After permeabilization, the extract isolated from plant stem cells or induced pluripotent stem cells is introduced into the adult-derived cells through the process of incubating the cells with the extract.

The present invention includes producing cells which are very similar to embryonic stem cells, that is, cells having the same genetic background and pluripotency as those of embryonic stem cells, through the process of culturing the cells to which the extract is introduced.

The present invention may further include culturing the adult-derived cells in a general cell culture after introducing the extract, and then transferring and culturing the adult-derived cells on a feeder cell layer.

More specifically, adult-derived cells to which the extract is introduced are cultured in a usual cell medium (DMEM, 10% FBS, 50 U/ml penicillin, 50 mg/ml streptomycin) until a colony is formed after the process of introduction of the extract. After the colony is formed, the adult-derived cells are transferred onto a feeder cell layer and cultured while the adult-derived cells are subcultured every seven days and the medium is replaced by a fresh one every day. The feeder cell according to the embodiment of the present invention includes STO cells.

The pluripotent stem cells induced by the extract may be cultured in a culture solution in which Dulbecco's modified eagle medium (DMEM)/F12, a 20% knockout serum replacement (KSR), 2 mM L-glutamine, 0.1 mM non-essential amino acids, 0.1 mM β-mercaptoethanol, 50 U/ml penicillin, 50 mg/ml streptomycin and 10 ug/ml bFGF are added. It will be easily appreciated by those skilled in the art that the concentration of the compound added to the DMEM may be changed within the range in which the effect of the present invention may be achieved.

Further, the present provides a method of inducing customized pluripotent stem cells, including: a) producing an extract from any of plant stem cells or induced pluripotent plant stem cells; b) introducing the extract into adult-derived cells; and c) culturing the adult-derived cells in a general cell culture, transferring the adult-derived cells onto a feeder cell layer, and culturing the adult-derived cells in an embryonic stem cell medium.

When the method according to the embodiment of the present invention is used, cells which are very similar to embryonic stem cells may be produced from adult-derived cells by using plant stem cells or induced pluripotent plant stem cells.

The inventors of the present invention determined that customized pluripotent plant stem cells were induced using the method according to the embodiment of the present invention.

More specifically, it may be determined that the pluripotent stem cells induced according to the present invention are indistinguishable from embryonic stem cells in terms of morphology (refer to FIG. 4). Further, the pluripotent stem cells induced according to the present invention were determined to express the genes Nanog and Oct4 which are hallmarks of embryonic stem cells (refer to FIG. 7). Further, the present invention provides customized pluripotent stem cells induced using the method according to the embodiment of the present invention.

The inventors of the present invention successively performed a subculture 10 times, and thereby determined the self-renewal of the pluripotent stem cells, which is one of the characteristics of stem cells (refer to FIG. 6).

Further, the present invention provides a cell therapy agent including the customized pluripotent stem cells according to the embodiment of the present invention. More specifically, the cell therapy agent may be used to form hepatocytes, adipocytes, osteocytes, chondrocytes, myocytes, neurons, cardiomyocytes, vascular endothelial cells, etc.

As used herein, the term "cell therapy agent" refers to a medicine, prepared by isolating from humans, culturing and specially manipulating human cells or tissues, for use in the treatment, diagnosis and prevention of a disease (US FDA regulations), that is, a medicine, prepared by a series of processes of proliferating and selecting autologous, homologous or heterologous cells in vitro or changing biological properties of cells to rehabilitate the function of cells or tissues, for use in the treatment, diagnosis and prevention of a disease. The cell therapy agents are classified into adult somatic cell therapy agents and stem cell therapy agents according to the degree of differentiation of cells, and the present invention relates to a therapy agent for stem cells.

Hereinafter, the present invention will be described in detail in conjunction with the following examples. However, the following examples merely exemplify the present invention, and the present invention is not limited to the following examples.

Example 1. Introduction of Extract of Plant Stem Cells into Adult-Derived Cells

The inventors of the present invention used a callus powder as an extract of plant-derived stem cells. The type of the callus powder which may be used in the present invention is not limited. Sequoia callus powders provided from Amorepacific Corporation were used in the following examples.

More specifically, human dermal fibroblast cells were harvested with trypsin-EDTA and washed with cold phosphate buffered saline (PBS). The cell pellet thus obtained was resuspended in a cold $Ca^{2+}$- and $Mg^{2+}$-free Hank's balanced salt solution (HBSS) (concentration of 100,000 cells/100 µl) and was transferred to 1.5 ml tubes. After centrifugation at 120 g at 4° C. for 5 minutes in a swing-out rotor, a supernatant was discarded, and the resulting cell pellet was resuspended in 97.7 µl of cold HBSS and incubated at 37° C. for 2 minutes in a water bath. 2.3 µl of streptolysin O (SLO; diluted (1:10) in cold HBSS to a concentration of 100 g/mL) was added to the reaction solution (final SLO concentration: 230 ng/mL). Further, digitonin (20 ug/ml) and 200 ul of a transport solution (110 mM potassium acetate, 5 mM sodium acetate, 2 mM magnesium acetate, 1 mM EGTA, 2 mM DTT, a protease-inhibitor cocktail, 20 mM HEPES pH 7.3) may be added instead of SLO in the above-described process. The sample was incubated for 50 minutes in a 37° C. water bath during which it was turned upside down once every ten minutes. The incubated sample was put on ice and 200 µl of cold HBSS was added thereto, followed by centrifugation at 120 g at 4° C. for 5 minutes in a swing-out rotor. After the permeabilization, the cell pellet was resuspended at a density of 1000 cells/µl in 200 µl of the extract of the plant stem cells. Callus powders were used as the extract of the plant stem cells (500 ug/ml). Thereafter, an ATP-regeneration system (10 mM creatine phosphate and 25 g/ml creatine kinase) and 1 mM of each of the nucleotide triphosphates were added to the suspension, followed by incubation for 1 hour in a 37° C. water bath while turning upside down once every ten minutes. After the incubation, 1 ml of an ES cell medium containing 2 mM $CaCl_2$ was added to the suspension, and the suspension was incubated for 2 hours in a 37° C. incubator to reseal plasma membranes. The cells were washed with PBS, resuspended in the embryonic stem cell culture medium, and seeded on a 0.1% gelatin-coated dish.

Example 2. Preparation of Cells Similar to Embryonic Stem Cells by Culturing Extract-Introduced Cells The cells were cultured at 37° C. in a general cell culture medium in which 10% FBS, 50 U/ml penicillin, 50 mg/ml streptomycin are added to Dulbecco's modified eagle medium (DMEM) in a 5% $CO_2$ incubator. Adult-derived cells (human dermal fibroblast cells) to which the extract of plant stem cells (callus powder) was introduced on a 0.1% gelatin-coated dish were cultured in the above-described medium which was replaced by a fresh one after incubating for the first two days. After the medium was replaced by a fresh one every day and the cells were cultured for 10 days, the cells were divided into two groups at a ratio of 1:2 per dish and cultured on a mitomycin C (MMC)-treated feeder cell layer. Thereafter, the cells were cultured in a medium in which 20% knockout serum replacement (KSR), 2 mM L-glutamine, 0.1 mM non-essential amino acids, 0.1 mM β-mercaptoethanol, 50 U/ml penicillin, 50 mg/ml streptomycin, 10 ug/ml bFGF were added to Dulbecco's modified eagle medium (DMEM)/F12, while the medium was replaced by a fresh one every day, and the cells were transferred to a fresh feeder cell layer at a regular interval of 7 days. On average, customized stem cells required for analysis could be cultured on about the 21th day of culturing.

Figure 1:
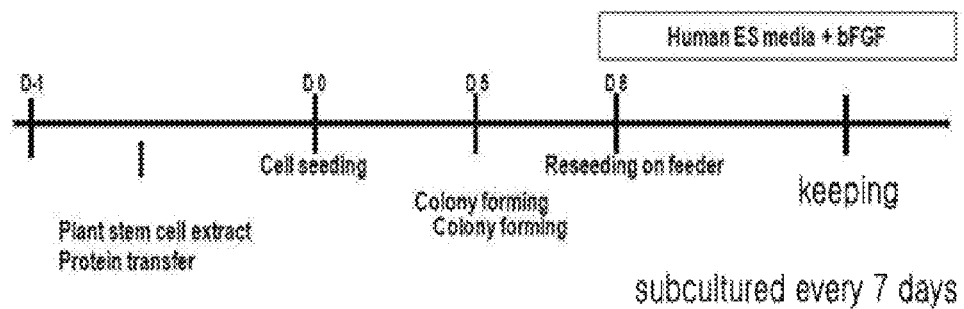
FIG. 1 is a schematic view illustrating the overall procedure of inducing customized pluripotent stem cells according to the method of present invention.
Figure 2:
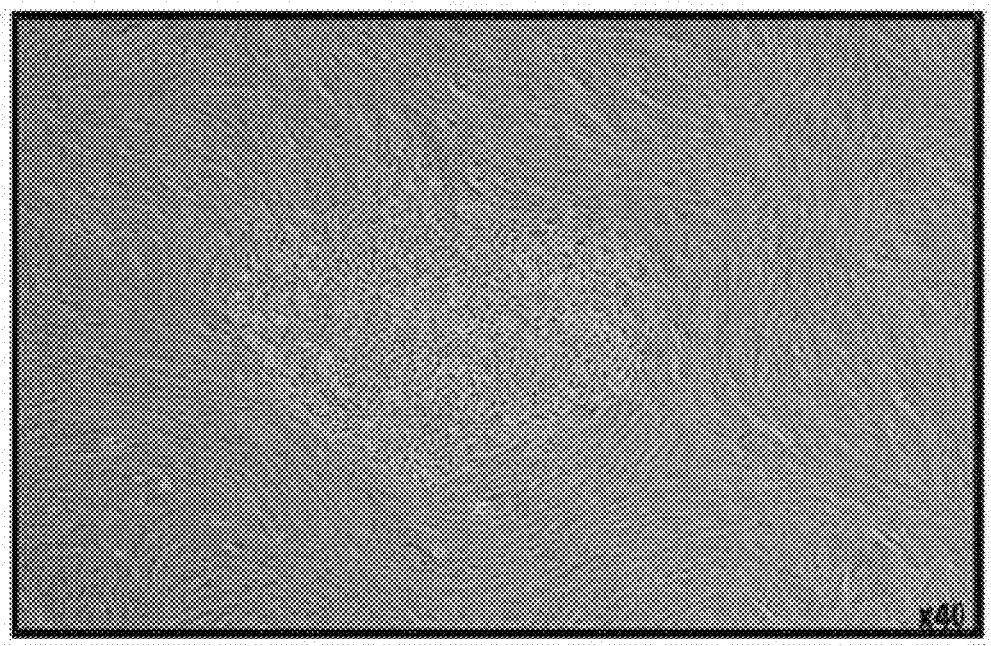
FIG. 2 is a view illustrating induced pluripotent stem cells on day 5 after treatment with an extract of plant stem cells.
Figure 3:
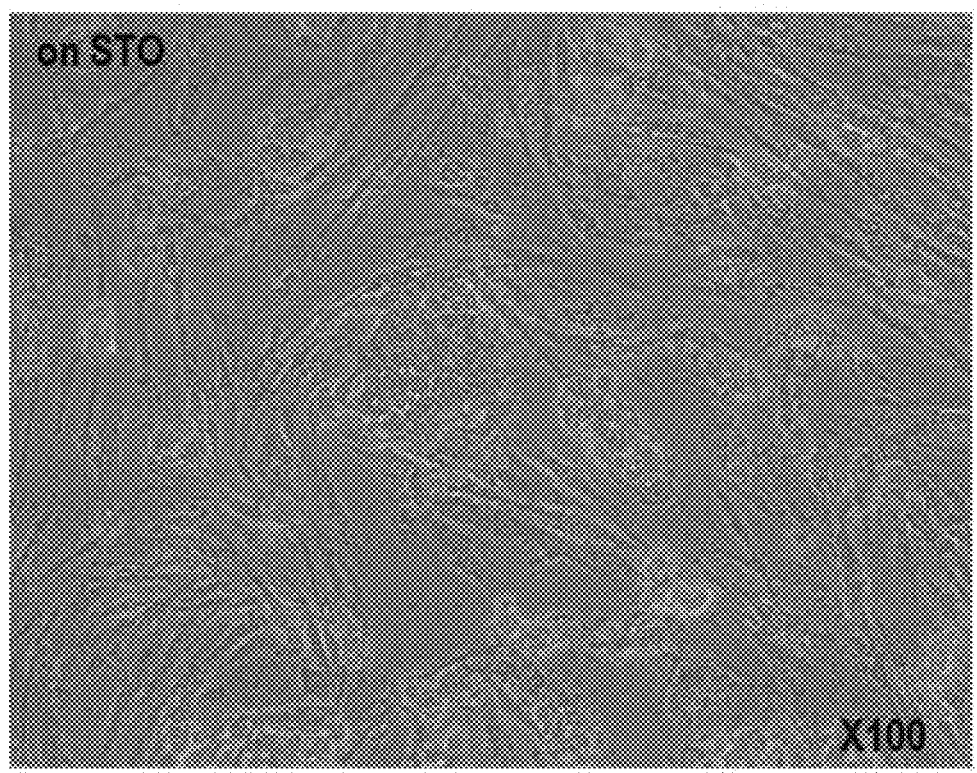
FIG. 3 is a view illustrating induced pluripotent stem cells on day 8 after treatment with an extract of plant stem cells and day 2 after being transferred onto a feeder cell layer.

FIG. 1 is a schematic view illustrating the overall procedure of inducing customized pluripotent stem cells according to the method of present invention. FIGS. 2 to 4 show the pluripotent stem cells induced on the 5th day, 10th day and 32th day, respectively. FIGS. 5 and 6 show alkaline phosphatase staining of the pluripotent stem cells on the 32th day and 50th day of culture, respectively. Alkaline phosphatase staining was observed using a general staining kit.

As shown in FIG. 6, the pluripotent stem cells induced according to the method of the present invention were observed to be positive to alkaline phosphatase staining (purple), like embryonic stem cells.

Example 3. Characterization Analysis of Customized Pluripotent Stem Cells (Gene Expression Analysis)

After collecting the cultured cells, total RNA was isolated using a TRIzol reagent (Invitrogen). After a reverse transcription polymerase chain reaction (RT-PCR) was performed to synthesize cDNA, PCR was performed with respect to primers specific to Nanog, Oct-3/4, and a control gene GAPDH. The PCR products were analyzed by agarose gel electrophoresis, and the results are shown in FIG. 7.

As shown in FIG. 7, it may be determined that Nanog and Oct-3/4, which are hallmark genes of embryonic stem cells (hES), were expressed in the induced pluripotent stem cells (hiPS) according to the method of the present invention.

The above description about the present invention is merely for exemplifying, and it is to be appreciated that those skilled in the art can easily change or modify the embodiments without departing from the scope and spirit of the present invention. Therefore, it should be understood that the foregoing embodiments are provided only for purposes of illustration and not in any way as limiting the present invention.

INDUSTRIAL APPLICABILITY

According to the embodiment of the present invention, customized pluripotent stem cells which raise no ethical issue and ensure safety can be produced.

The invention claimed is:

1. A method of producing induced stem cells, comprising:
pre-treating human dermal fibroblasts with a membrane permeability-promoting material;
contacting a Sequoia callus extract with the pre-treated human dermal fibroblasts such that at least part of the Sequoia callus extract is permeated into the pre-treated human dermal fibroblasts, which provides modified human cells containing at least part of the Sequoia callus extract;
culturing, in a culture medium, the modified human cells containing at least part of the Sequoia callus extract, which produces induced stem cells expressing Nanog and Oct-3/4; and
subsequently collecting at least part of the induced stem cells expressing Nanog and Oct-3/4.

2. The method of claim 1, wherein the Sequoia callus extract comprises proteins, lipids, sugars and acids of callus of Sequoia.

3. The method of claim 1, wherein the method further comprises mixing the Sequoia callus extract with the culture medium before contacting the Sequoia callus extract with the human dermal fibroblasts.

4. The method of claim 1, wherein the Sequoia callus extract contacts the pre-treated human dermal fibroblasts in the form of suspension in water and has a concentration of 100 ug/ml to 1 mg/ml.

5. The method of claim 4, wherein the concentration is 500 ug/ml.

6. The method of claim 1, wherein the Sequoia callus extract is in powder.

7. The method of claim 6, wherein the powder of the Sequoia callus extract is dissolved in water before contacting the pre-treated human dermal fibroblasts.

8. The method of claim 1, wherein the membrane permeability-promoting material includes streptolysin O.

9. The method of claim 1, wherein the membrane permeability-promoting material includes digitonin.

10. The method of claim 1, wherein culturing comprises transferring the modified human cells containing at least part of the Sequoia callus extract onto a surface of feeder cells.

11. The method of claim 10, wherein the feeder cells comprise STO cells.

12. The method of claim 10, wherein the culture medium comprises a Knockout serum replacement.

13. The method of claim 10, wherein subsequent to transferring, the modified human cells containing at least part of the Sequoia callus extract are cultured on the surface of the feeder cells, wherein the culture medium comprises a Knockout serum replacement, wherein culturing in the culture medium is performed subsequent to culturing on the surface of the feeder cells.

14. The method of claim 1, wherein the culture medium comprises a Knockout serum replacement.

* * * * *